United States Patent [19]

Lange

[11] Patent Number: 4,645,664

[45] Date of Patent: Feb. 24, 1987

[54] MICROPOROUS POWDER FORM POLYLACTIDES

[75] Inventor: Wolfgang Lange, Obernburg, Fed. Rep. of Germany

[73] Assignee: AKZO, NV, Arnhem, Netherlands

[21] Appl. No.: 761,106

[22] Filed: Jul. 31, 1985

[30] Foreign Application Priority Data

Aug. 3, 1984 [DE] Fed. Rep. of Germany ....... 3428640

[51] Int. Cl.$^4$ .................... A61K 31/74; C08G 63/08
[52] U.S. Cl. .................................. 424/78; 528/354; 528/491
[58] Field of Search ................... 424/78; 528/354, 491

[56] References Cited

U.S. PATENT DOCUMENTS

| | | | |
|---|---|---|---|
| 4,137,921 | 2/1979 | Okuzumi et al. | 528/354 |
| 4,157,437 | 6/1979 | Okuzumi et al. | |
| 4,247,498 | 1/1981 | Castro | 264/49 |

FOREIGN PATENT DOCUMENTS

| | | |
|---|---|---|
| 0026599 | 4/1981 | European Pat. Off. |
| 3218150 | 11/1983 | Fed. Rep. of Germany |
| 3218151 | 11/1983 | Fed. Rep. of Germany |

OTHER PUBLICATIONS

Polymer 1979, vol. 20, pp. 1459–1464.

*Primary Examiner*—Joseph L. Schoffer
*Assistant Examiner*—Peter F. Kulkosky
*Attorney, Agent, or Firm*—Michael J. Striker

[57] ABSTRACT

A microporous powder form polylactide which can take up a multiple of its own weight of active material and which can be used for the controlled release of that active material. The aforesaid microporous polylactide powder can be prepared by dissolving polylactide under warming in phthalicacid diethylester, preferably at a temperature over 150° C. and then slowly cooling the clear solution. The resulting suspension is then subjected to filtering and any remain phthalicacid diethylester preferably removed by extraction. The microporous powder recovered is especially suitable for applying thereto therapeutically active substances for controlled release therefrom and is particularly suitable for utilization in veterinary and human medicine. The microporous powder in this form can be introduced into the body subcutaneously, intramuscularly and intraperitoneally.

16 Claims, No Drawings

MICROPOROUS POWDER FORM POLYLACTIDES

BACKGROUND OF THE INVENTION

This invention relates to microporous powder foam (pulverulent) polylactides, a process for manufacturing the same as well as their use as controlled release agents and more particularly their use for controlled release of therapeutically effective substances.

Polylactides have been known for some time. They can be employed as homopolymers as well as in the form of copolymers with different substances. Polylactides are in general biologically degradable and when introduced into the human or animal body, over the course of time they are degraded to harmless chemical substances. As a result, the interest in the polylactides as formed bodies or powder foam particles has in recent times increased considerably. An important objective sought to be achieved is the provision of microporous tricklable polylactide powders which are suitable (adapted) for taking up large amounts of active substances and of then releasing such substances into the surrounding millieu over a prolonged period of time.

Up until the present, there has been lacking a process for making polylactides in powder form which are microporous and which can then take up into their pores the active agents. Under the use of known solvents such as benzene or toluene, polylactide solutions are prepared which permit the formation of solid bodies as well as films and foils. Powders which are microporous and which are suitable for use to carry active agents are however not obtained with solvents such as benzene and toluene.

In DE-OS No. 32 18 151, a process is described for preparing microporous, powder form polylactides according to which polylactide is dissolved in xylene, the resulting clear solution is cooled and the xylene separated off. With this process there are obtained true microporous powders which are capable of storing or taking up active substrates. The disadvantage of this process is that the product obtained exhibits a sheet like or scale like structure which for the intended use presents considerable disadvantages. It would be advantageous in this connection for the polylactide powder particles to have rounded spherical-like shapes.

It is an object of the invention to provide microporous, powder form polylactides which do not have the aforenoted disadvantages and which display a rounded spherical-like shape which can in a simple manner be charged or loaded with active materials and which are then able to release this active material into the surrounding environment over a prolonged period of time.

Another object of this invention is to provide microporous powder form polylactide particles which can be loaded or charged with small or large amounts of active substance and which in this form are suitable for use in veterinary and human medicine.

A further object of this invention is to provide microporous powder form polylactide particles which can be loaded or charged with small or large amounts of active substance and which in this form are suitable for use in agriculture, for plant growth and pest control.

Still another object of the invention is to provide a process for manufacturing the aforesaid powder form particles.

These objects are realized in accordance with the process of the invention for the manufacture of microporous, powder form particles which comprises dissolving polylactide in phthalicacid diethylester under application of heat, cooling the resulting solution and separating off the phthalicacid diethylester. Preferably, the polylactide is dissolved at a temperature above 150° C. After the cooling has taken place, the phthalicacid diethylester can be separated off from the polylactide powder by suction and extraction with ethanol. Preferably, in the preparation of the solution 50 to 60 parts of polylactide and 85 to 45 of phthalicacid diethylester are used.

It is advantageous if the polylactide solution is cooled at a rate of 20° to 200° C. per minute down to room or ambient temperature. The cooled mixture is then allowed to stand for long period and preferably for 90 minutes or more and then the resultant suspension is filtered.

As polylactides, there can be used in this process polymers of dl-lactic acid, 1(+)-lactic acid, d(−)-lactic acid alone or in mixtures. Particularly suitable are copolymers of one of the aforementioned lactic acids with another hydroxycarboxylic acid. As such hydroxycarboxylic acid, glycollic acid is preferred.

The microporous powder form polylactide particles which are obtained or made available by the aforedescribed process are novel and constitute an important aspect of this invention.

These microporous powder form polylactides which are obtained according to the invention are particularly suitable for the controlled release of therapeutically active substances into the animal or human body and can be introduced for this purpose intraperitoneally, intramuscularly and subcutaneously.

As polylactide starting material, in the sense of the invention, there are understood to be suitable all of the homo- and copolymers of lactic acid including of d(−)-lactic acid, 1(+)-lactic acid and dl-lactic acid as well. For manufacturing the copolymers, glycollic acid is particularly suitable.

Preferably biologically degradable polylactides are used. Suitable polylactides are for instance described in Polymer 1979, Vol. 20, page 1459–1464. Also in the patent literature, there are to be found numerous disclosures regarding the preparation of polylactides. As examples of such patents describing the preparation of the polylactides there may be mentioned EP OS No. 26 599 and U.S. Pat. No. 4,157,437.

The preparation of the solution of polylactide and phthalicacid diethylester can be effected in a simple manner as for example from mixing of the components and heating, preferably to a temperature above 150° C. It is recommended that the polylactide be provided in finely divided form and that dissolution be carried out under stirring. After only a short time, a clear solution is obtained. In the case of the presence of impurities which are not soluble, it is recommended that prior to the cooling, the solution containing such impurities be filtered. The hot solution is then slowly cooled. The cooling can be carried out for instance by allowing the solution to stand at room temperature until it has completely cooled down. It is also possible to carry out the cooling at a rate of about 20° C. to 200° C. per minute. The cooled mixture is then allowed to stand for some time preferably for about 90 minutes. Depending on the concentration and quality of the polylactide used, there is then obtained a suspension or a more or less crumbly mass which still contains phthalicacid diethylester. A substantial part of the phthalicacid diethylester can be separated off from the polylactide through filtering or suction. The remaining crumbly material is extracted with a suitable liquid which is effective to dissolve the phthalic acid diethylester but not the polylactide. For this purpose ethanol is especially suitable. As examples of other suitable extraction liquids, there may be mentioned isopropanol, methanol and the like. For the extraction, it has been found particularly advantageous to use a conventional extraction apparatus such as the Soxhlet apparatus. The extraction fluid which remains on the particles can then through simple drying under mild conditions be separated off. The now recovered crumbly mass can then in a simple way, as for example, by passing through a screen or mesh be converted into the corresponding pulverulent i.e., powder form. A mill is not necessary.

There are obtained pulverulent powder form particles with rounded spherical shapes which are tricklable. The greatest amounts of the particles i.e. approximately 75-80 weight percent are in the range of particles having diameters of 100-200 μm.

The recovered powders present on the basis of their microporous structure no problems to being loaded or charged with different active substances. A very suitable method of applying such active substances is by using aqueous solutions of for example an antibiotic. Because the powders are hydrophillic and because of the capillary action of the micropores, the solution of active agents is quickly taken up by the particles. Through drying, for example, under reduced pressure it is possible to very quickly separate off the solving agent i.e., water, so that the powder is now depo having solid active agents deposited therein and therein.

Through the option of concentrating the aqueous solution of active agents, it is possible to vary the content of active agent in the powder. It is also possible to treat the powders one or more times with the active agent solution so that it is possible to fill the entire available hollow space of the powders with active agent. In this way, through multiple treatments with aqueous solutions of active agent the final content of active agent can be increased. As the powders of the invention have very high hollow pore volumes, i.e., over 60 volume percent up to a maximum of about 85 volume percent, it is possible according to the instant invention that a polylactide product can be obtained which holds up to about 85 volume percent of solid active agent. The powder can thus contain many times its own weight of the active agent.

It is to be understood that the microporous powders can also be filled with non aqueous solutions of active agents. Thus it is possible to use organic solvents and therewith also to obtain very high amounts of active agents.

It is also possible that the active agent itself will be a liquid so that without the use of water or a nonaqueous solvent, the active material can be charged into the mircoporous powders.

It was especially surprising that it was possible in accordance with the invention to manufacture microporous tucklable polylactide powders which can be charged with large amounts of active agents of different types such as medicaments, polypeptides, hormones, antibiotics, vitamins, etc. as well as pesticides, herbicides, trace elements, fragrances, etc. for storage thereof and for releasing the same into the surrounding environment over a prolonged period of time. That the microporous polylactide powders are also self-degradable is in connection with their use in human and animal bodies very important and provides special advantages for the micropowders of the invention.

The polylactide powders can when they have been loaded with active agents be used directly in this form. They can also, for example, be pressed to form shaped bodies such as tablets or thin rods or bars. It is to be understood that it is also possible to prepare the powders directly with the designated body shape and then in this form to charge them with the active agent. In a particularly advantageous method of proceeding, the solid or liquid, active agent charged polymer according to the invention is distributed in a matrix of degradable polymer. In this way it is possible to manufacture further combinations with different degradation velocities and controlled release properties. The manufacture of this type of combination is described in DE-OS No. 32 18 150.

Polylactide powders which have been charged with suitable active agents can be used in both human and animal medicine and they can be introduced into the body of human or animal subcutaneously, intraperitoneally, or intramuscularly.

The microporous polylactide powders release in the course of time into animal or human body their content of active agent and are then themselves after some time biodegraded to nontoxic substances in the body.

It is also possible for the shaped bodies such as the small rods or bars to be inserted into certain areas of the body as for example under the skin, for instance in the fat layers where they serve as a depot for the release of active agents.

They can also be used in agriculture, and in forestry for instance, in the prevention of pests such as insects and to great advantage as plant growth regulating agents.

The chemical composition of the polymers vary over a wide range so that their degradability and velocity of their degradability in the various environments can be adjusted. The type of active agent can also thereby be varied so that the manner of use of the microporous powders of the invention can be adjusted in many aspects. It is also understood that there may be used more than one active agent at a time for realizing a multiplicity of effects.

The following example serves to further illustrate the invention but is in no way to be construed as limitative of the scope thereof.

EXAMPLE

Preparation of Polylactide Powder 300 g l-polylactide (homopolymer of l-lactid acid) were dissolved in 76.3 weight percent phthalicacid diethylester at 160° C. by stirring for 90 minutes. The clear solution which was formed was then poured into tins to a layer thickness of 2 to 5 mm. After 90 minutes of standing time, the resulting suspension was attrited and washed with ethanol a multiple number of times. Following three hours of drying in a vacuum dryer at 50° C., a white tucklable powder having the following particle size distribution was obtained:

| Fraction (μm) | Part % |
|---|---|
| 400 | 0 |
| 400–315 | 0 |

-continued

| Fraction (μm) | Part % |
|---|---|
| 315–200 | 14.58 |
| 200–100 | 78.03 |
| 100–80 | 5.73 |
| 80–50 | 0 |
| 50 | 1.65 |
| | 100.0 |

In order to load the powdery particles with active material, 20 g l-polylactide powder were treated under stirring at room temperature with 7 ml of an ethanolic solution containing 800 mg acetylsalicylic acid, the addition taing place over a 10 minute period. After completion of the addition of the solution, the powder-solution mixture was stirred for an additional 30 minutes. Thereafter over a 60 minute period, 30 l $N_2$/hr were conducted over the powder in order to dry it. After repeating this step 5 more times, the powdery product has a loading content of about 20% acetylsalicylic acid.

I claim:

1. Process for the preparation of microporous, substantially spherical and tricklable, powder form polylactide which comprises dissolving polylactide in phthalic acid diethylester under application of heat, cooling the resultant clear solution, separating off the phthalic acid diethylester and recovering the microporous powder form polylactide.

2. Process according to claim 1, which comprises dissolving the polylactide in said phthalicacid diethylester at a temperature over 150° C.

3. Process according to claim 1, which comprises separating off the phthalicacid diethylester by suction and extraction with ethanol.

4. Process according to claim 1, which comprises utilizing 15 to 60 parts polylactide and 85 to 40 parts phthalicacid diethylester for forming the solution.

5. Process according to claim 1, which comprises cooling the polylactide solution at a rate of 20° to 200° C. per minute down to room temperature, allowing the cooled solution to stand about 90 minutes and then filtering the resulting suspension.

6. Process according to claim 1, which comprises utilizing as the polylactide polymer, a dl-lactic acid polymer, a d(−)-lactic acid polymer or l(+)-lactic acid polymer alone or in admixture.

7. Process according to claim 1, which comprises utilizing as the polylactide polymer a copolymer of lactic acid with another hydroxycarboxylic acid.

8. Process according to claim 7, wherein as hydroxycarboxylic acid, glycollic acid is used.

9. A microporous, substantially spherical and tricklable, powder form polyactide prepared according to the process of claim 1.

10. A microporous, substantially spherical and trickable, powder form polylactide according to claim 9 having a particle size of from about 50 to about 400 μm.

11. A microporous, substantially spherical and tricklable, powder form polylactide according to claim 9 adapted for use as a controlled release agent.

12. A microporous, substantially spherical and tricklable, powder form polylactide according to claim 11 loaded with a therapeutic active agent effective for use in veterinary and human medicine.

13. Method for the controlled release of therapeutically active agent which comprises introducing the microporous, substantially spherical and tricklable, powder form polylactide according to claim 12 into a human or animal body for release of the therapeutically active agent therein.

14. Method for the controlled release of therapeutically active agent which comprises subcutaneously introducing the microporous, substantially spherical and tricklable, powder form polylactide according to claim 12 into a human or animal.

15. Method for the controlled release of therapeutically active agent which comprises intramuscularly introducing the microporous, substantially spherical and tricklable, powder form polytactide according to claim 12 into a human or animal.

16. Method according to claim 15, wherein said active agent is a member selected from the group consisting of medicaments, polypeptides, hormones, antibiotics, and vitamins.

* * * * *